US009949849B2

(12) United States Patent
Maitland

(10) Patent No.: US 9,949,849 B2
(45) Date of Patent: Apr. 24, 2018

(54) MEDIAL-LATERAL STABILIZING PROSTHETIC ANKLE/FOOT FOR ANGLED AND ROUGH GROUND GAIT

(71) Applicant: UNIVERSITY OF WASHINGTON THROUGH ITS CENTER FOR COMMERCIALIZATION, Seattle, WA (US)

(72) Inventor: Murray E. Maitland, Seattle, WA (US)

(73) Assignee: University of Washington Through its Center for Commercialization, Seattle, WA (US)

(*) Notice: Subject to any disclaimer, the term of this patent is extended or adjusted under 35 U.S.C. 154(b) by 10 days.

(21) Appl. No.: 14/781,511

(22) PCT Filed: May 14, 2014

(86) PCT No.: PCT/US2014/037990
§ 371 (c)(1),
(2) Date: Sep. 30, 2015

(87) PCT Pub. No.: WO2014/186457
PCT Pub. Date: Nov. 20, 2014

(65) Prior Publication Data
US 2016/0058581 A1 Mar. 3, 2016

Related U.S. Application Data

(60) Provisional application No. 61/823,130, filed on May 14, 2013.

(51) Int. Cl.
*A61F 2/66* (2006.01)
*A61F 2/50* (2006.01)

(52) U.S. Cl.
CPC .............. *A61F 2/66* (2013.01); *A61F 2/6607* (2013.01); *A61F 2002/5009* (2013.01); *A61F 2002/6614* (2013.01); *A61F 2002/6657* (2013.01)

(58) Field of Classification Search
CPC .. A61F 2/60; A61F 2/66; A61F 2/6607; A61F 2002/6614; A61F 2002/6621;
(Continued)

(56) References Cited

U.S. PATENT DOCUMENTS 5,258,039 A * 11/1993 Goh ........................ A61F 2/66
623/52
5,800,568 A * 9/1998 Atkinson ................. A61F 2/66
623/52
(Continued)

FOREIGN PATENT DOCUMENTS

EP 1068844 A1 1/2001
WO 2003/092543 A2 11/2003

OTHER PUBLICATIONS

Wiersdorf, Jason Matthew. Preliminary Design Approach for Prosthetic Ankle Joints Using Compliant Mechanisms. Bringham Young University All Theses and Dissertations. Paper 721. 2005.*
(Continued)

*Primary Examiner* — Thomas J Sweet
*Assistant Examiner* — Christie Bahena
(74) *Attorney, Agent, or Firm* — McDonnell Boehnen Hulbert & Berghoff LLP

(57) ABSTRACT

A device is provided including a first linkage system and a second linkage system. Each linkage system may include an upper support, a lower support, and a cross bar linkage including a first cross bar and a second cross bar. The first cross bar may be configured with a first end pivotally coupled to a first end of the lower support and a second end pivotally coupled to a second end of the upper support. The second cross bar may be configured with a first end pivotally coupled to a second end of the lower support and a second end pivotally coupled to a first end of the upper support. The device may also include a flexible bridging platform coupled to one of the upper support or the lower support of the first linkage system and coupled to the upper support of the second linkage system, and a flexible strut coupled to the lower support of the second linkage system.

14 Claims, 13 Drawing Sheets

(58) Field of Classification Search
CPC ...... A61F 2002/6628; A61F 2002/6635; A61F 2002/6642; A61F 2002/665; A61F 2002/6657; A61F 2002/6664; A61F 2002/6671; A61F 2002/6678; A61F 2002/6685; A61F 2002/6692; A61F 3/00
See application file for complete search history.

(56) References Cited

U.S. PATENT DOCUMENTS

| | | | |
|---|---|---|---|
| 5,824,112 A * | 10/1998 | Phillips | A61F 2/66 623/52 |
| 5,944,760 A | 8/1999 | Christensen | |
| 2008/0109084 A1 | 5/2008 | Maitland | |
| 2013/0118287 A1* | 5/2013 | Holgate | B25J 17/00 74/490.01 |

OTHER PUBLICATIONS

Derwent Abstract of DE29920434. Goemed Orthopaedie-Service. Published Apr. 6, 2000.*
Earthwalk. Fitting and Adjusting The Earthwalk 2 Flexible Keel Foot and Ankle. Ohio Willow Wood. Nov. 9, 2010.*
Peacock, et al., "The Incidence and Health Economic Burden of Ischemic Amputation in Minnesota, 2005-2008," Prev Chronic Dis, 2011; 8(6): A141.
Schaper, et al., "Reducing lower leg amputations in diabetes: a challenge for patients, healthcare providers and the healthcare system," Diabetologia (2012) 55:1869-1872.
International Search Report for PCT/US2014/037990, dated Sep. 16, 2014.

* cited by examiner

MEDIAL-LATERAL STABILIZING PROSTHETIC ANKLE/FOOT FOR ANGLED AND ROUGH GROUND GAIT

CROSS-REFERENCE TO RELATED APPLICATIONS

This application is a U.S. national phase of International Application No. PCT/US2014/037990, filed on May 14, 2014, which claims benefit of U.S. Provisional Application No. 61/823,130, filed May 14, 2013, both of which are incorporated by reference herein in their entirety.

BACKGROUND

Unless otherwise indicated herein, the materials described in this section are not prior art to the claims in this application and are not admitted to be prior art by inclusion in this section.

In the normal ankle and foot there is an anatomical kinematic chain from the ankle joint to the toes. In particular, a normal foot has a series of articulations with increasing levels of motion, including the talocural (ankle) joint, the subtalar (heel) joint, the tarsal (midfoot) joint, and the metatarsals and phalanges (forefoot). The sequence of the articulations of a normal foot permit variations in lateral motions depending on the surface coming into contact with the foot, or the position of the body above the foot. When lower extremity amputations result due to abnormal development, trauma, diabetes, or some other medical condition, these amputations of the leg or ankle result in chronic disability. This is because conventional prosthetic foot designs do not sufficiently replace the anatomical function of the foot to accommodate sideways motions.

SUMMARY

Example devices described herein allow adaptation of a prosthetic foot in the medial-lateral direction, including pronation and supination of the prosthetic foot. The device described herein may mimic the functions of a normal foot using a series of articulations. Articulations are permitted in the disclosed devices due to linkage systems positioned at various locations of the prosthetic foot, as described in more detail below. The disclosed devices may improve walking, running, and other forms of bipedal motion (such as dancing) for people with prosthetic feet. In particular, the disclosed devices may allow for level placement of the leg over the foot on uneven ground or a medial-lateral grade during walking and running. The disclosed devices may further accommodate variations in leg position over the foot for a person with poor coordination. In addition, the disclosed devices may permit variations in leg position on a level surface for people participating in various recreational activities such as dance or racquet sports. Robotic prostheses may also benefit from the mechanical adaptations of the invention to make them more versatile and functional.

Thus, in one aspect, a device is provided including (a) a first linkage system and a second linkage system, each linkage system may include (i) an upper support, (ii) a lower support, and (iii) a cross bar linkage including a first cross bar and a second cross bar, where the first cross bar may be configured with a first end pivotally coupled to a first end of the lower support and a second end pivotally coupled to a second end of the upper support, and the second cross bar may be configured with a first end pivotally coupled to a second end of the lower support and a second end pivotally coupled to a first end of the upper support, (b) a flexible bridging platform coupled to one of the upper support or the lower support of the first linkage system and coupled to the upper support of the second linkage system, where the plane of rotation of the lower support of the first linkage system may be substantially parallel to the plane of rotation of the lower support of the second linkage system, and (c) a flexible strut coupled to the lower support of the second linkage system.

In a second aspect, the device may further include (d) a third linkage system, including (i) an upper support, (ii) a lower support, and (iii) a cross bar linkage including a first cross bar and a second cross bar, where the first cross bar may be configured with a first end pivotally coupled to a first end of the lower support and a second end pivotally coupled to a second end of the upper support, the second cross bar may be configured with a first end pivotally coupled to a second end of the lower support and a second end pivotally coupled to a first end of the upper support, the upper support of the first linkage system may be coupled to the flexible bridging platform and the lower support of the third linkage system may be coupled to one of the flexible bridging platform or the upper support of the first linkage system, and the plane of rotation of the lower support of the third linkage system may be substantially perpendicular to the plane of rotation of the lower support of the first and second linkage systems.

In a third aspect, another device is provided including (a) a hindfoot support, (b) an ankle support including a first linkage system, (c) a forefoot support including a second linkage system, and (d) a flexible bridging platform, where a top surface of the flexible bridging platform is coupled to a lower surface of the first linkage system, and a bottom surface of the flexible bridging platform is coupled to an upper surface of the second linkage system and an upper surface of the hindfoot support.

These as well as other aspects, advantages, and alternatives, will become apparent to those of ordinary skill in the art by reading the following detailed description, with reference where appropriate to the accompanying drawings.

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, with respect to measurements, "about" means+/−5%.

As used herein, "weighted height" means the height of a component when a downward force is applied to a surface of the component.

As used herein, "unweighted height" means the height of a component when no downward force is applied to a surface of the component.

Standing atop a typical artificial leg without medial-lateral accommodation to the ground surface is analogous to standing on stilts. The long lever-arm of the leg falls outside of the base of support without much angle at the base. Example devices described herein may allow adaptation of a prosthetic foot in the medial-lateral direction, including pronation and supination of the prosthetic foot. The device described herein may mimic the functions of a normal foot using a series of articulations. The articulations may be permitted via linkage systems positioned at various locations of the prosthetic foot, as described in more detail with reference to the figures below.

Figure 1:
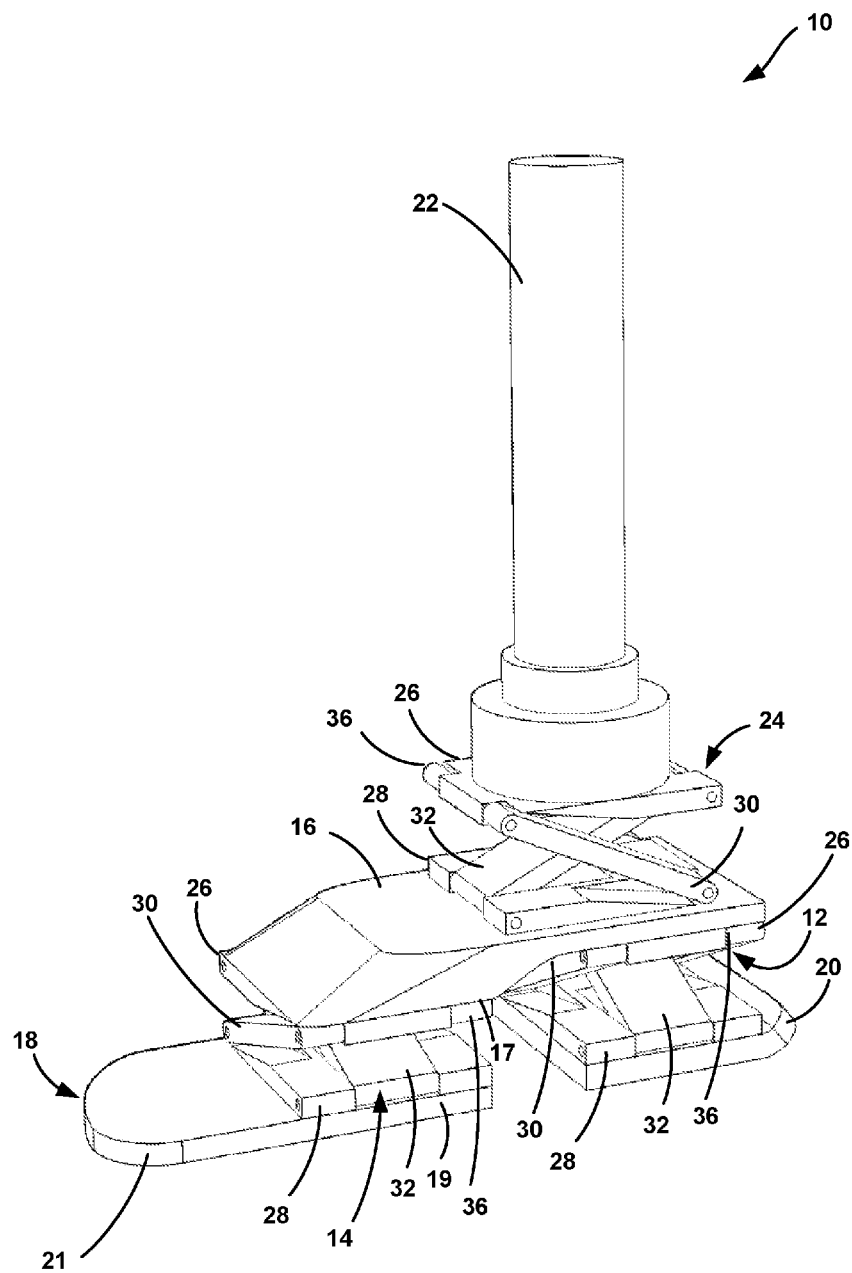
FIG. 1 is a perspective view of a prosthetic device, according to one example embodiment.

In a first aspect, FIG. 1 illustrates an example prosthetic device 10 in accordance with one embodiment of the invention. The prosthetic device 10 may include a first linkage system 12 and a second linkage system 14. The first linkage system 12 may be a hindfoot component of the prosthetic device 10, and the second linkage system 14 may be a forefoot component. The plane of rotation of the first linkage system 12 may be substantially parallel to the plane of rotation of the second linkage system 14. In other words, like components of the first linkage system 12 and the second linkage system 14 are facing the same direction, as shown in FIG. 1.

The prosthetic device 10 may also include a flexible bridging platform 16 coupling the first linkage system 12 to the second linkage system 14. The flexible bridging platform 16 may include carbon fiber, a carbon fiber composite, a high density nylon material, or combinations thereof, amongst other possibilities. The flexible bridging platform 16 may mimic a tarsal joint (midfoot) of a normal foot to supply a balance of rigidity and spring to the foot function. As weight moves from hindfoot to forefoot, the midfoot flexible bridging platform 16 accommodates unevenness between the front and back ground level, as well as the angle of the user's leg relative to the floor. As the wearer of the prosthetic device 10 shifts their weight forward, the flexible bridging platform 16 may act as a springboard propelling the wearer forward in bipedal motion. In one example, the flexible bridging platform 16 may have a level bottom surface, such that the top surface of the first linkage system 12 and the top surface of the second linkage system 14 are substantially parallel. In another example, such as the example shown in FIG. 1, the flexible bridging platform 16 may have a two-tiered bottom surface 17. The two-tiered bottom surface 17 of the flexible bridging platform 16 may cause the unweighted height of the second linkage system 14 to be less than the unweighted height of the first linkage system 12. Such a configuration may be advantageous for fitting the prosthetic device 10 in a shoe, as an example. The preferred position of the two-tiered bottom surface 17 of the bridging platform 16 may be adjusted based on the particular user, and the particular footwear of the user. For example, higher heeled shoes will need more angulation of the two-tiered bottom surface 17. Other configurations are possible as well.

The prosthetic device 10 may further include a flexible strut 18 coupled to a lower support of the second linkage system 14. The flexible strut 18 may include a forefoot pad 19 coupled to the lower support of the second linkage system 14 and a flexible toe pad 21 extending from the lower support of the second linkage system 14 in a direction away from the first linkage system 12. The flexible strut 18 may include carbon fiber, a carbon fiber composite, a high density nylon material, or combinations thereof, among other possibilities. The first linkage system 12 may include a hindfoot pad 20 coupled to a lower support of the first linkage system 12. The hindfoot pad 20 may include a rounded end as shown in FIG. 1 to ease bipedal motion and accommodate a user's heel strike against the ground.

In one example, a prosthetic limb 22, such as a shank, may be coupled to the flexible bridging platform 16, in a position above the first linkage system 12. A bottom portion of the prosthetic limb 22 may include a connector portion that is configured to mate with a connector portion positioned on the flexible bridging platform 16. Other connection mechanisms are possible as well.

In another example, such as the configuration shown in FIG. 1, a third linkage system 24 may be positioned between the flexible bridging platform 16 and the prosthetic limb 22. The third linkage system 24 may have a similar configuration to the first linkage system 12 and the second linkage system 14. However, the plane of rotation of the third linkage system 24 may be substantially perpendicular to the plane of rotation of the first linkage system 12 and the plane of rotation of the second linkage system 14. In such a configuration, the first linkage system 12 and the second linkage system 14 may enable medial-lateral movement, such as pronation and supination of the foot. The third linkage system 24 may enable dorsiflexion and plantarflexion of the foot. The upper support of the first linkage system 12 may be coupled to the flexible bridge 16, as described above. The lower support of the third linkage system 24 may be coupled to either the flexible bridging platform 16 or the upper support of the first linkage system 12.

In a configuration including the third linkage system 24, the prosthetic limb 22 may be coupled to the upper support of the third linkage system 24. A bottom portion of the prosthetic limb 22 may include a connector portion that is configured to mate with a connector portion positioned on a top surface of the upper portion of the third linkage system 24. Other connection mechanisms are possible as well.

The prosthetic device 10 may further include a housing sized and shaped to receive the prosthetic device 10. For example, the housing may be a shoe that encompasses the prosthetic device 10. In another example, the housing may be shaped like a human foot. Other examples are possible as well.

Figure 2:
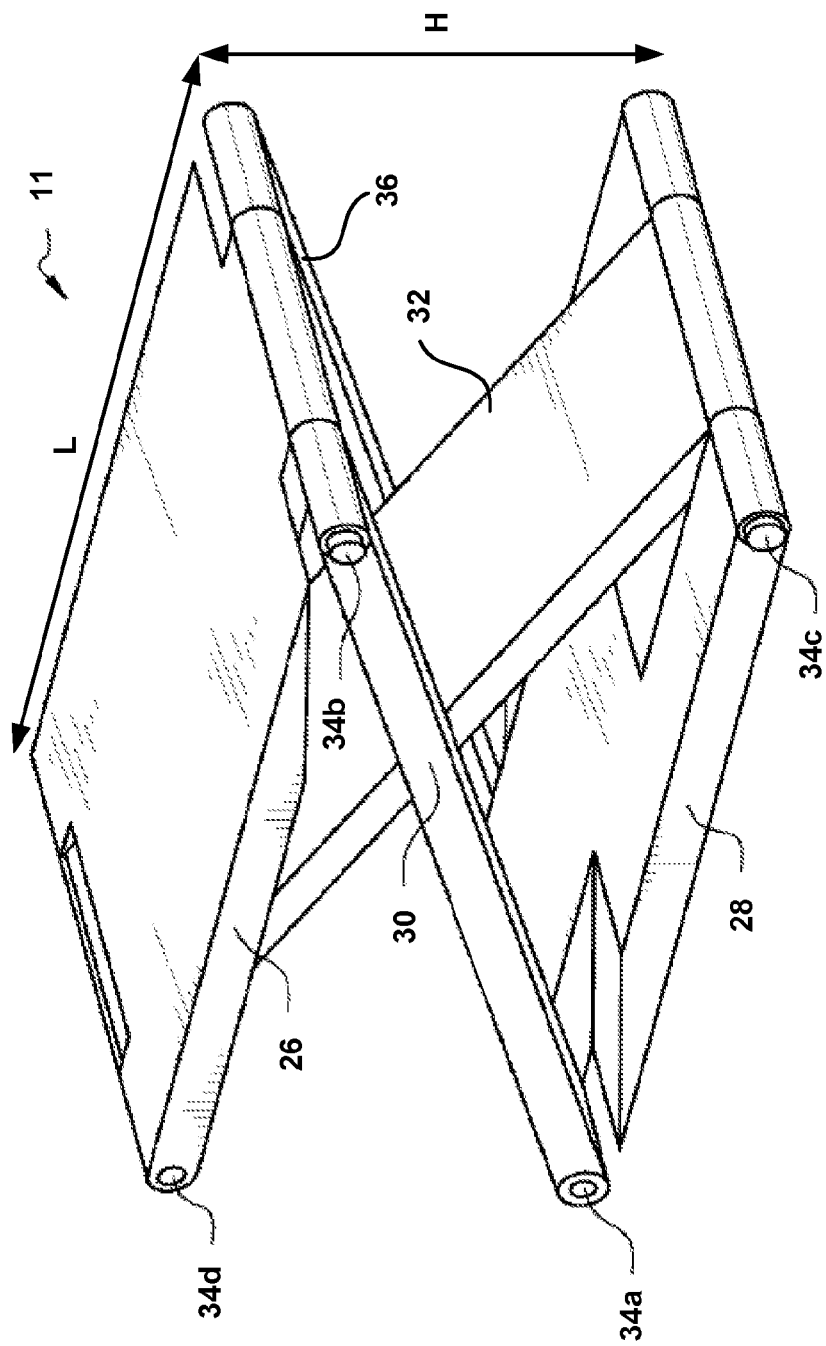
FIG. 2 is a perspective view of a linkage system of the prosthetic device, according to an example embodiment.

FIG. 2 illustrates an example linkage system 11 of the prosthetic device 10. The first linkage system 12, the second linkage system 14, and the third linkage system 24 may be configured similarly to the linkage system 11 shown in FIG. 2. The linkage system 11 may include an upper support 26 and a lower support 28. The linkage system 11 may further include a cross bar linkage including a first cross bar 30 and a second cross bar 32. The first cross bar 30 may be configured with a first end pivotally coupled to a first end of the lower support 28 and a second end pivotally coupled to a second end of the upper support 26. Similarly, the second cross bar 32 may be configured with a first end pivotally coupled to a second end of the lower support 28 and a second end pivotally coupled to a first end of the upper support 26. The first end of the first cross bar 30 may be pivotally coupled to the first end of the lower support 28 via axle 34a, and the second end of the first cross bar 30 may be pivotally coupled to the second end of the upper support 26 via axle 34b. The axles 34a, 34b may be configured to pass through a hole in the lower support 28 and upper support 26, respectively, and corresponding holes in the first cross bar 30. Similarly, the first end of the second cross bar 32 may be pivotally coupled to the second end of the lower support 28 via axle 34c, and the second end of the second cross bar 32 may be pivotally coupled to the first end of the upper support 26 via axle 34d.

In some examples, such as the example shown in FIG. 2, the cross bar linkage of the linkage system 11 may further include a third cross bar 36. Similar to the first cross bar 30, the third cross bar 36 may be configured with a first end pivotally coupled to a first end of the lower support 28 and a second end pivotally coupled to a second end of the upper support 26. The first end of the first cross bar 30 may be pivotally coupled to the first end of the lower support 28 via axle 34a, and the second end of the first cross bar 30 may be pivotally coupled to the second end of the upper support 26 via axle 34b. As shown in FIG. 2, the second cross bar 32 may be positioned between the first cross bar 30 and the second cross bar 36. Other potential linkage systems are possible as well.

Figure 3:
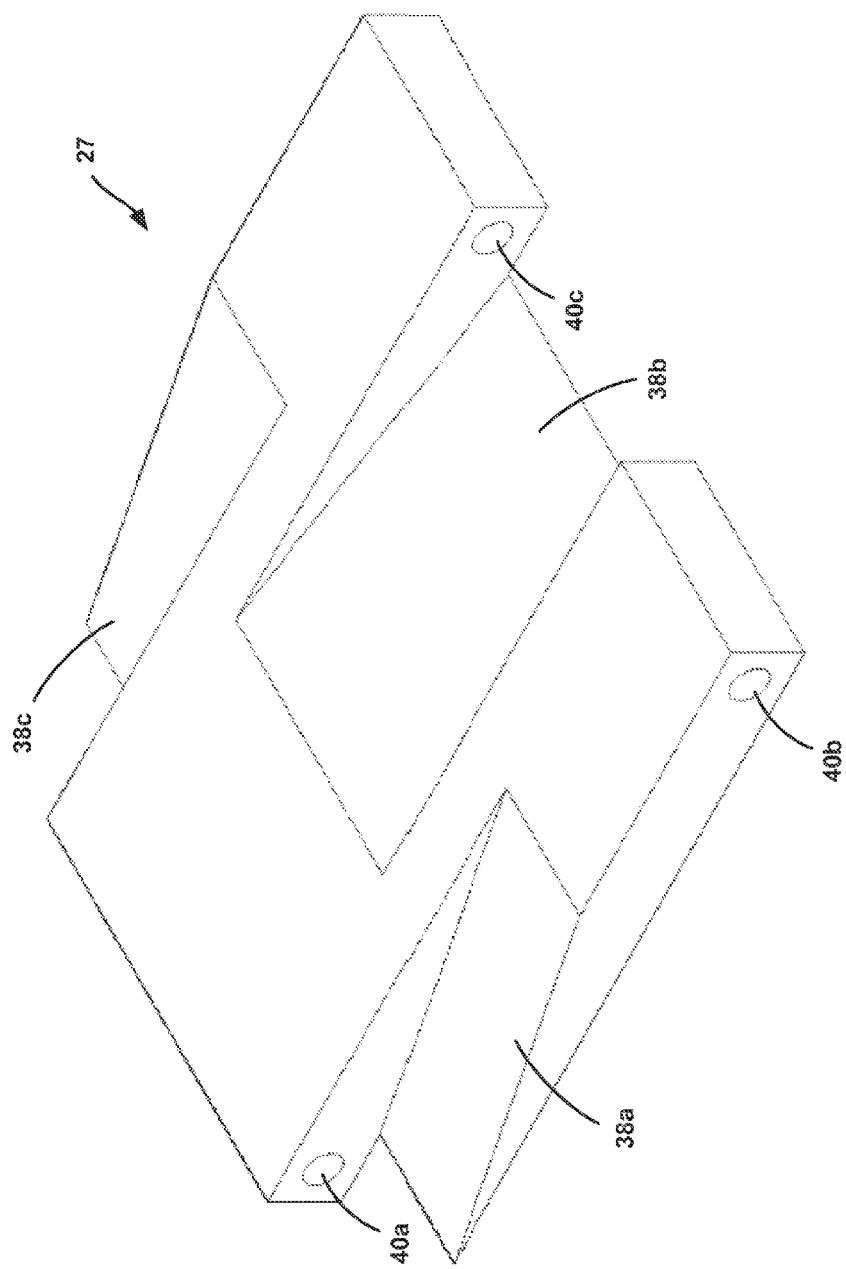
FIG. 3 is a perspective view of a support of the linkage system of the prosthetic device, according to the example embodiment of FIG. 1.

FIG. 3 illustrates a support of the linkage system 11. The support 27 shown in FIG. 3 may represent the upper support 26, the lower support 28, or both, since the upper support 26 and the lower support 28 may be substantially similar. The support 27 may include a first angled surface 38a, a second angled surface 38b, and a third angled surface 38c. The support may also include a first hole 40a, a second hole 40b, and a third hole 40c.

Figure 4A:
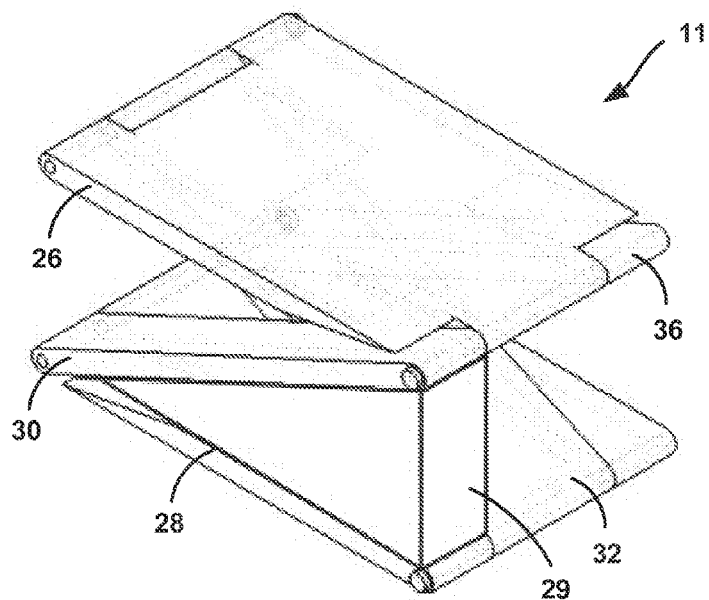
FIG. 4A is a side view of a linkage system of the prosthetic device including a compliant material, according to an example embodiment.
Figure 4B:
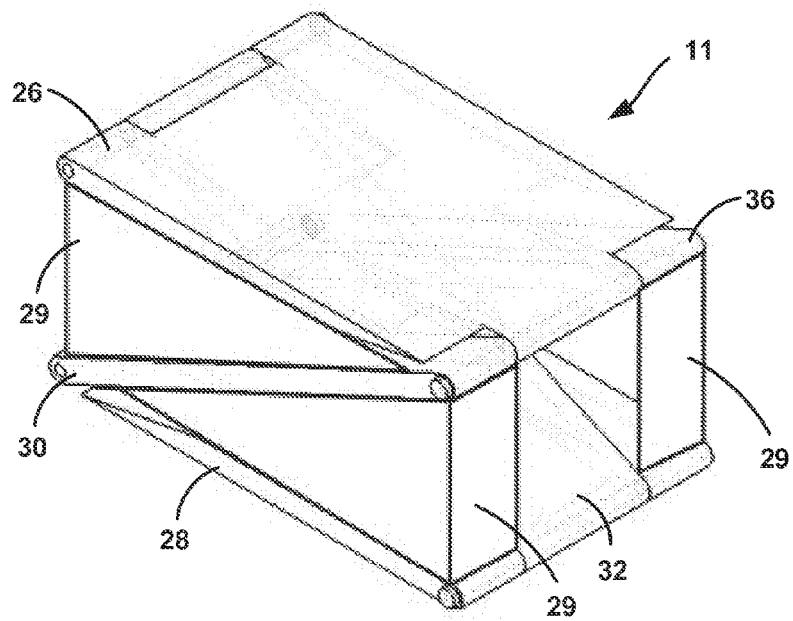
FIG. 4B is a side view of a linkage system of the prosthetic device including a compliant material, according to an example embodiment.
Figure 5:
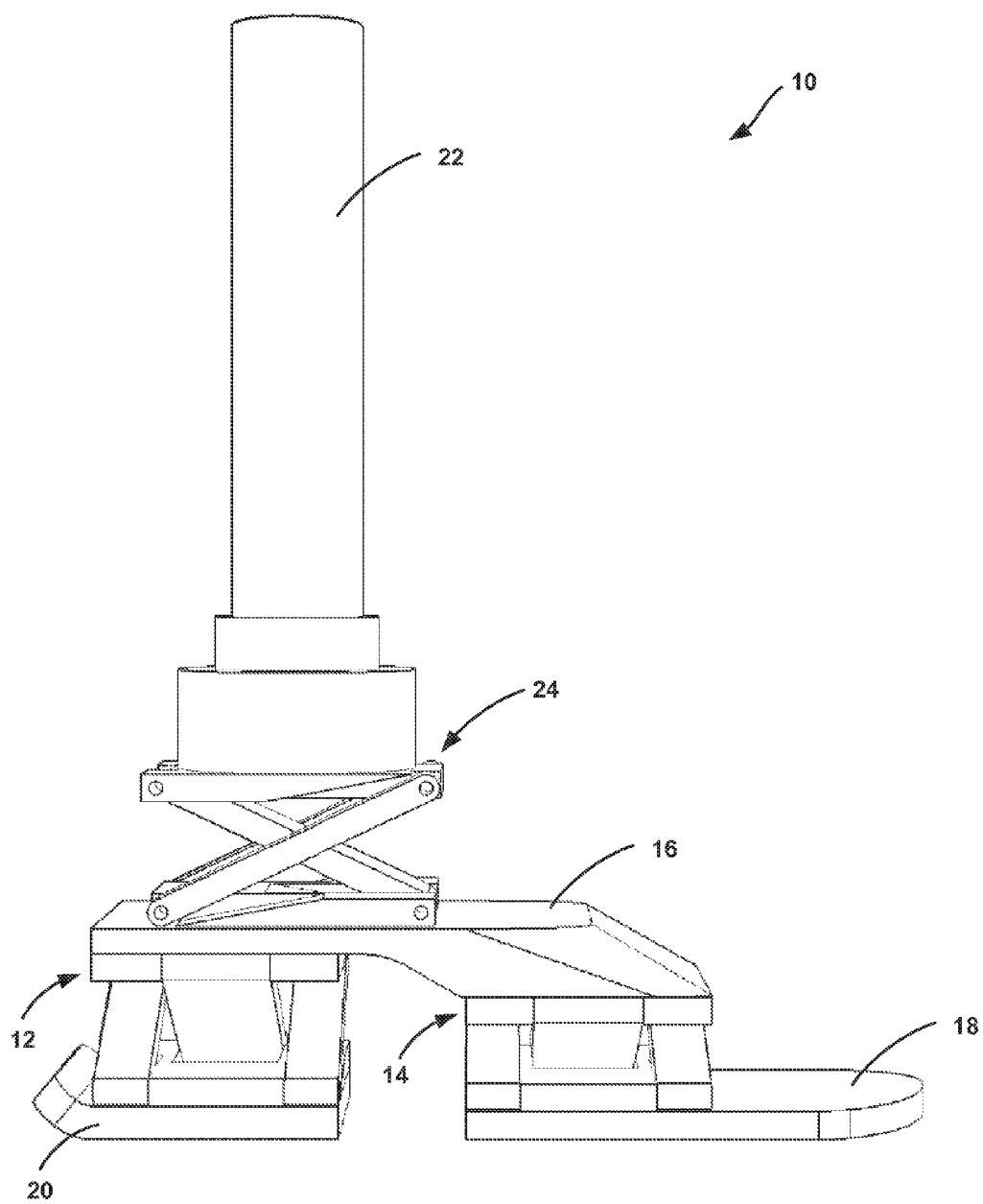
FIG. 5 is a side view of a prosthetic device, according to the example embodiment of FIG. 1.

FIGS. 4A and 4B illustrate another example embodiment, in which the linkage system 11 includes a compliant material 29 disposed between the upper support 26 and the lower support 28. The compliant material 29 may be configured to transition the linkage system 11 from a weighted height to an unweighted height. For example, in operation a wearer of the prosthetic device 10 may step on an inclined surface at an angle to the incline, as discussed in more detail below in relation to FIG. 7. In such a case, on one side of the linkage system 11, the lower support 28 moves closer to the upper support 26. At the same time on the opposite side of the linkage system 11, the upper support 26 moves further away from the lower support 28. As the wearer lifts the foot off of the inclined surface, the compliant material 29 may return or assist with returning the linkage system 11 to a position of repose before the wearer places the foot back on the ground. Further, the compliant material 29 may be used to modify rotational properties of the lower support 28 with respect to the upper support 26.

FIG. 4A illustrates one embodiment with a single compliant material 29 positioned between the first cross bar 30 and the lower support 28. Such a configuration would limit the rotation of the first cross bar 30. FIG. 4B illustrates another example embodiment, with multiple compliant materials positioned between various components of the linkage system 11. As shown in FIG. 4B, compliant material 29 is positioned between the first cross bar 30 and the lower support 28, the first cross bar 30 and the upper support 26, and the second cross bar 36 and the lower support 28. The complaint material may also be positioned between the second cross bar 36 and the upper support 26.

The length-to-height ratio of the linkage system 11 may vary. The length L and height H of the linkage system 11 is shown in FIG. 2. In one example, the length-to-height ratio may be less than 2:1 in an unweighted position. It is desirable to keep the center of rotation of the linkage system 11 relatively low, so as to keep the center of rotation within the base of support at the maximal angular position. The physical size of the linkage system 11 is scalable within the desired length-to-height ratio.

Figure 7:
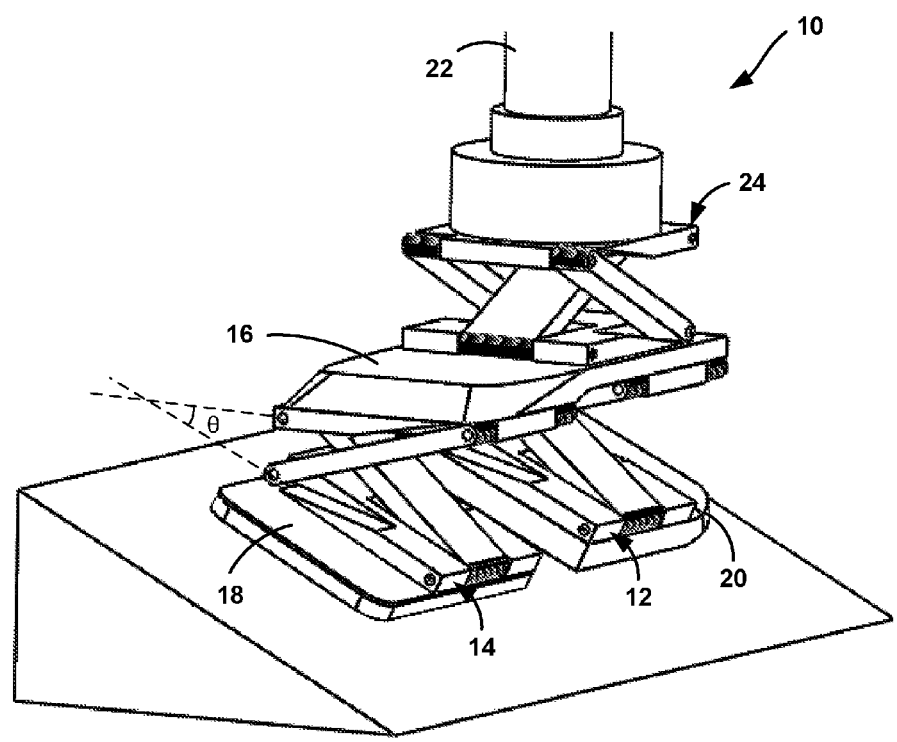
FIG. 7 shows a prosthetic device disposed on a medial-lateral grade, according to the example embodiment of FIG. 1.

As discussed above, each of the first linkage system 12, the second linkage system 14, and the third linkage system 24 described above in relation to FIG. 1 may have each of the components of linkage system 11. However, the linkage systems may be slightly different from one another. For example, the second linkage system 14 may have a shorter length and shorter unweighted height than the length and unweighted height of the first linkage system 12. Such a configuration may be advantageous for fitting the prosthetic device 10 in a shoe or other housing, as examples. In another example, each of the linkage systems may have varying length to height ratios to match their desired function in the prosthetic device 10. As another example, each linkage system may have a defined maximum rotation to better mimic their corresponding joints of a human foot. The compliant material 29 described above in relation to FIGS. 4A and 4B may be used to define the maximum rotation for each linkage system. For example, the maximum angle between the upper support of the first linkage system 12 and the lower support of the first linkage system 12 may be between about ten and twenty degrees. FIG. 7 illustrates an example angle (θ) between the upper support of the first linkage system 12 and the lower support of the first linkage system 12. The maximum angle (θ) represents a position in which one component of the linkage system 11 contacts another component such that rotation of the upper support for the linkage system 11 with respect to the lower support of the linkage system 11 is prevented. As another example, the maximum angle between the upper support of the second linkage system 14 and the lower support of the second linkage system 14 may be between about twenty-five and thirty-five degrees. Further, the maximum angle between the upper support of the third linkage system 24 and the lower support of the third linkage system 24 may be between about twenty-five and thirty-five degrees. In one example, the rotation of each of the linkage systems may be limited via a cushioned stop on the angled surfaces 38*a*, 38*b*, 38*c* of the support 27, although other mechanisms for limiting the rotation of the linkage systems are possible as well.

Figure 6:
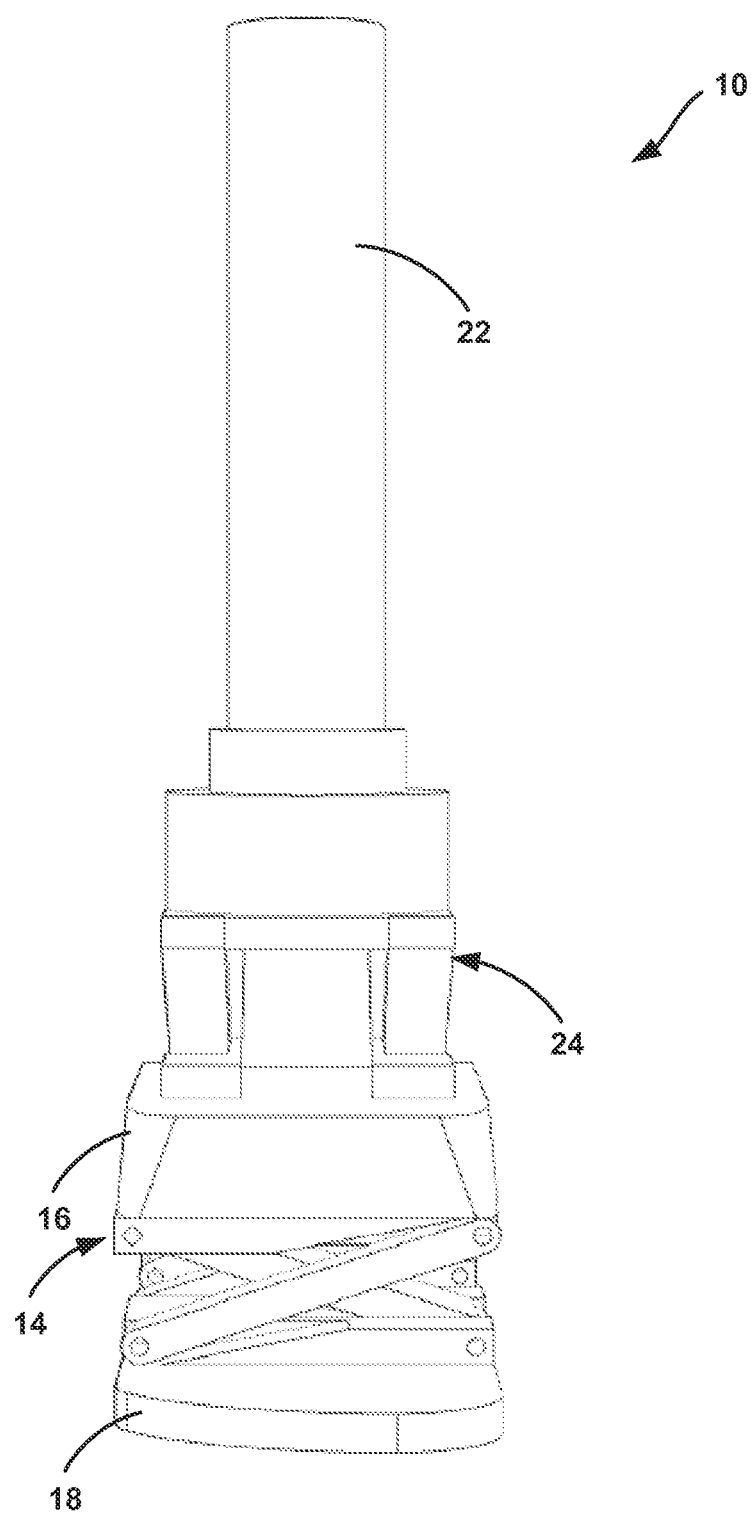
FIG. 6 is a front view of a prosthetic device, according to the example embodiment of FIG. 1.

FIG. 6 illustrates a side view of the prosthetic device 10 as described above, including the first linkage system 12, the second linkage system 14, the flexible bridging platform 16, the flexible strut 18, the hindfoot pad 20, the prosthetic limb 22 and the third linkage system 24. Similarly, FIG. 6 illustrates a front view of the prosthetic device 10, including the second linkage system 14, the bridging platform 16, the flexible strut 18, the prosthetic limb 22 and the third linkage system 24.

FIG. 7 illustrates the prosthetic device 10 on a medial-lateral grade, according to an example embodiment. As the flexible strut 18 and hindfoot pad 20 contacts uneven ground, the lower support of the first linkage system 12 and of the second linkage system 14 rotate, and becomes parallel to the ground surface. At the same time, the upper support of the first linkage system 12 and of the second linkage system 14 remain perpendicular to the prosthetic limb 22.

Figure 8:
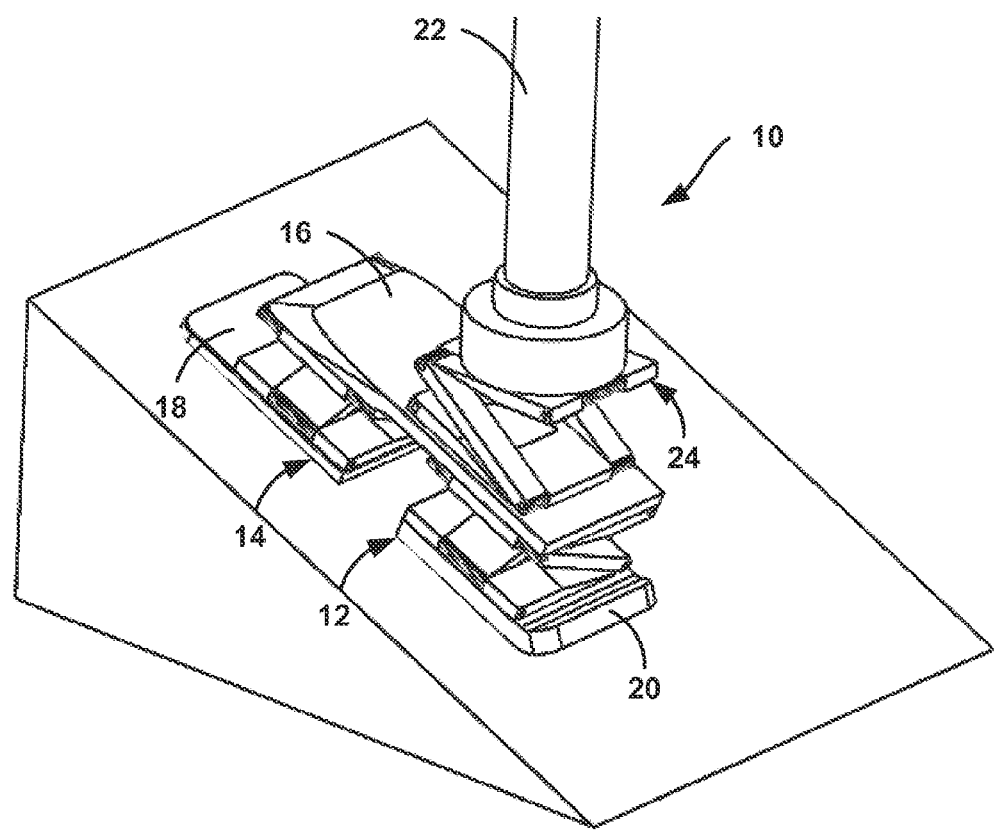
FIG. 8 shows a prosthetic device disposed on an incline, according to the example embodiment of FIG. 1.

FIG. 8 illustrates the prosthetic device 10 on an incline, according to an example embodiment. As the flexible strut 18 and hindfoot pad 20 contact the inclined ground, the lower support of the third linkage system 24 rotates, and becomes parallel to the inclined ground surface. The upper support of the third linkage system 24 remains perpendicular to the prosthetic limb 22.

Similarly, the prosthetic device 10 may help individuals having poor balance and gait. For example, the ground may be even but the prosthetic device 10 may come in contact with the ground at an angle due to poor balance and gait of the user. If the prosthetic device 10 contacts the ground in the medial-lateral direction, the lower support of the first linkage system 12 and the second linkage system 14 rotates, and becomes parallel to the ground surface, while the upper support of the first linkage system 12 and the second linkage system 14 remains perpendicular to the prosthetic limb 22. If the prosthetic device 10 contacts the ground in a dorsiflexion or plantarflexion position, the lower support of the third linkage system 24 may rotate, and become parallel to the inclined ground surface, while the upper support of the third linkage system 24 may remain perpendicular to the prosthetic limb 22.

Figure 9:
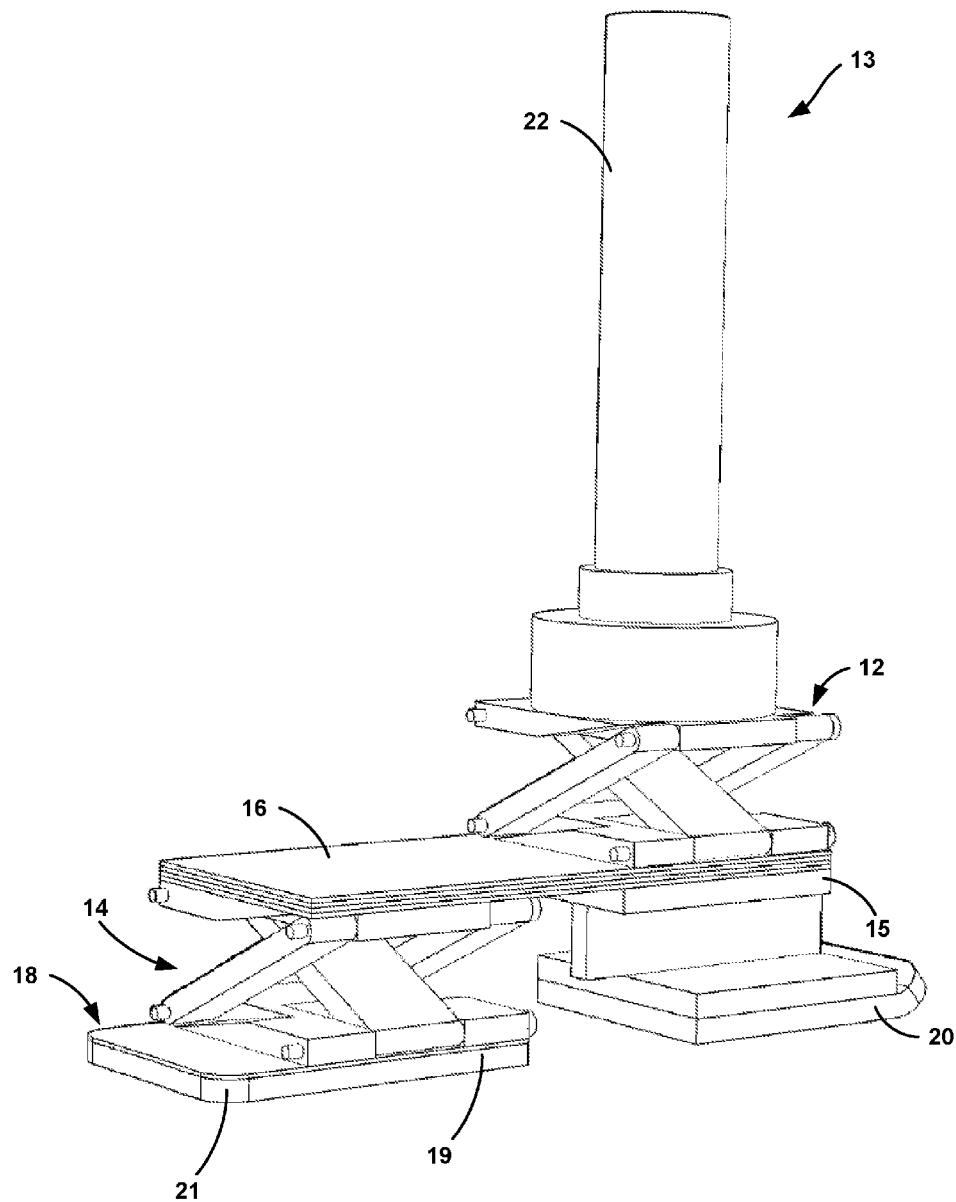
FIG. 9 is a perspective view of a prosthetic device, according to a second example embodiment.

FIG. 9 illustrates another prosthetic device 13 in accordance with another embodiment of the invention. The prosthetic device 13 may include a first linkage system 12 and a second linkage system 14. The first linkage system 12 and the second linkage system 14 may be configured similar to the linkage system 11 described above in relation to FIG. 2. The plane of rotation of the first linkage system 12 is substantially parallel to the plane of rotation of the second linkage system 14. In other words, the first linkage system 12 and the second linkage system 14 are facing the same direction, as shown in FIG. 9. The prosthetic device 13 may also include a flexible bridging platform 16 coupling the first linkage system 12 to the second linkage system 14. The lower support of the first linkage system 12 may be coupled to a top surface of the flexible bridging platform 16, and the upper support of the second linkage 14 may be coupled to a bottom surface of the flexible bridging platform 16.

The prosthetic device 13 may further include a flexible strut 18 coupled to a lower support of the second linkage system 14. The flexible strut 18 may include a forefoot pad 19 coupled to the lower support of the second linkage system 14 and a flexible toe pad 21 extending from the lower support of the second linkage system 14 in a direction away from the first linkage system 12. The flexible strut 18 may include carbon fiber, a carbon fiber composite, a high density nylon material, or combinations thereof, amongst other possibilities. Further, the prosthetic limb 22 may be coupled to the first linkage system 12. A bottom portion of the prosthetic limb 22 may include a connector portion that is configured to mate with a connector portion positioned on a top surface of the upper support of the first linkage system 12.

Figure 10:
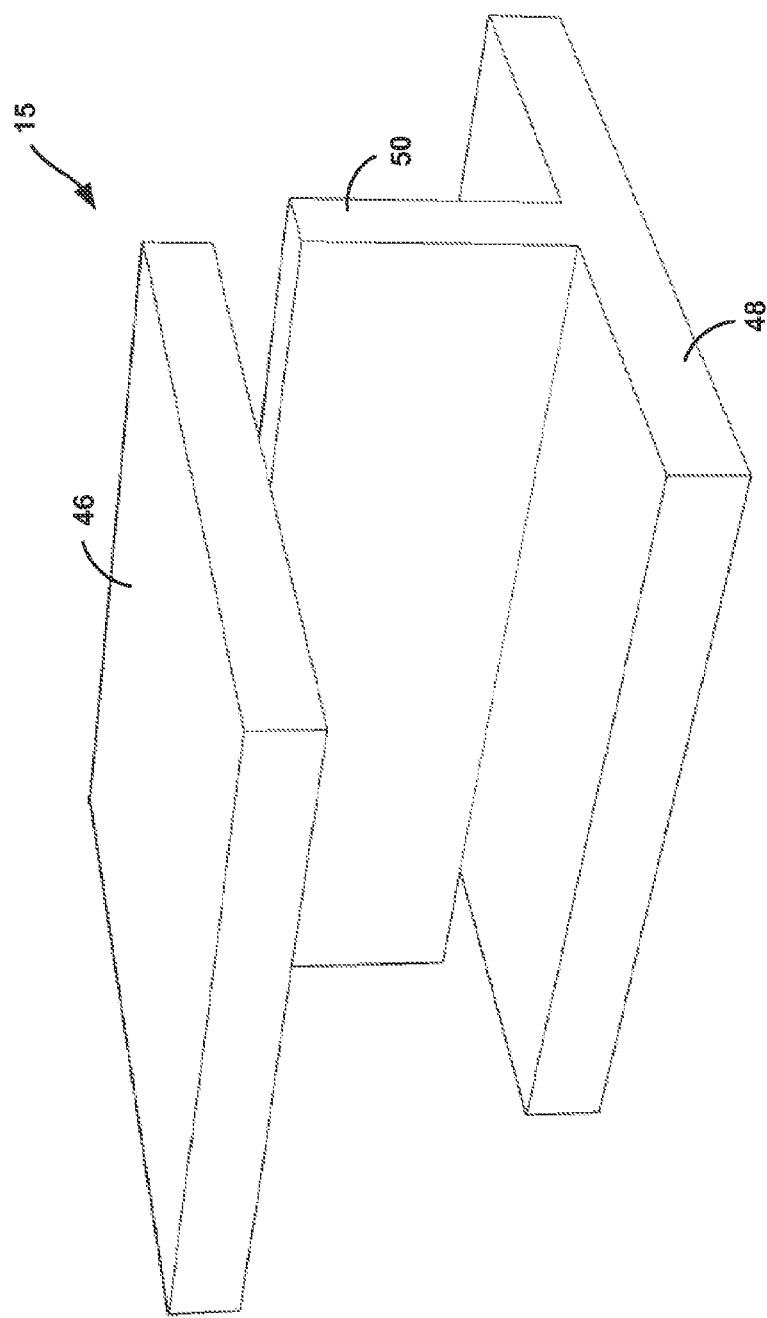
FIG. 10 is a perspective view of a hindfoot support of a prosthetic device, according to the example embodiment of FIG. 9.

The prosthetic device 13 may also include a hindfoot support 15 positioned under the first linkage system 12. FIG. 10 illustrates one example embodiment of the hindfoot support 15 in additional detail. As shown in FIG. 10, the hindfoot support 15 may be configured in the shape of an I-beam. In particular, hindfoot support 15 may include an upper flange 46, a lower flange 48, and a web portion 50. As shown in FIG. 10, the upper flange 46 may be offset from the edge of the lower flange 48 and the edge of the web portion 50. In addition, the web portion 50 may extend past the edge of the lower flange 48. The hindfoot support 15 may include a hindfoot pad 20 coupled to the lower flange 48 of the hindfoot support 15, as shown in FIG. 9. The hindfoot pad 20 may include a rounded end.

Figure 11:
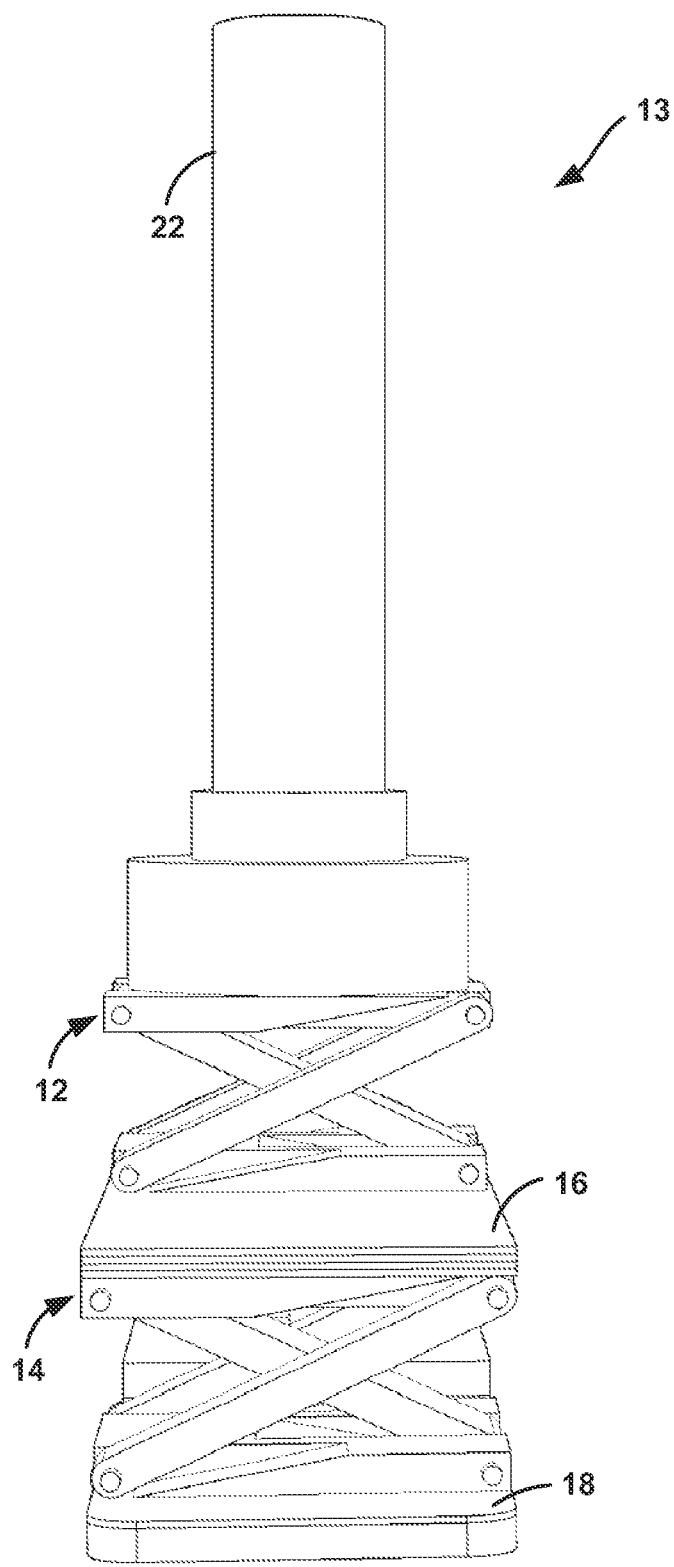
FIG. 11 is a front view of the prosthetic device, according to the example embodiment of FIG. 9.
Figure 12:
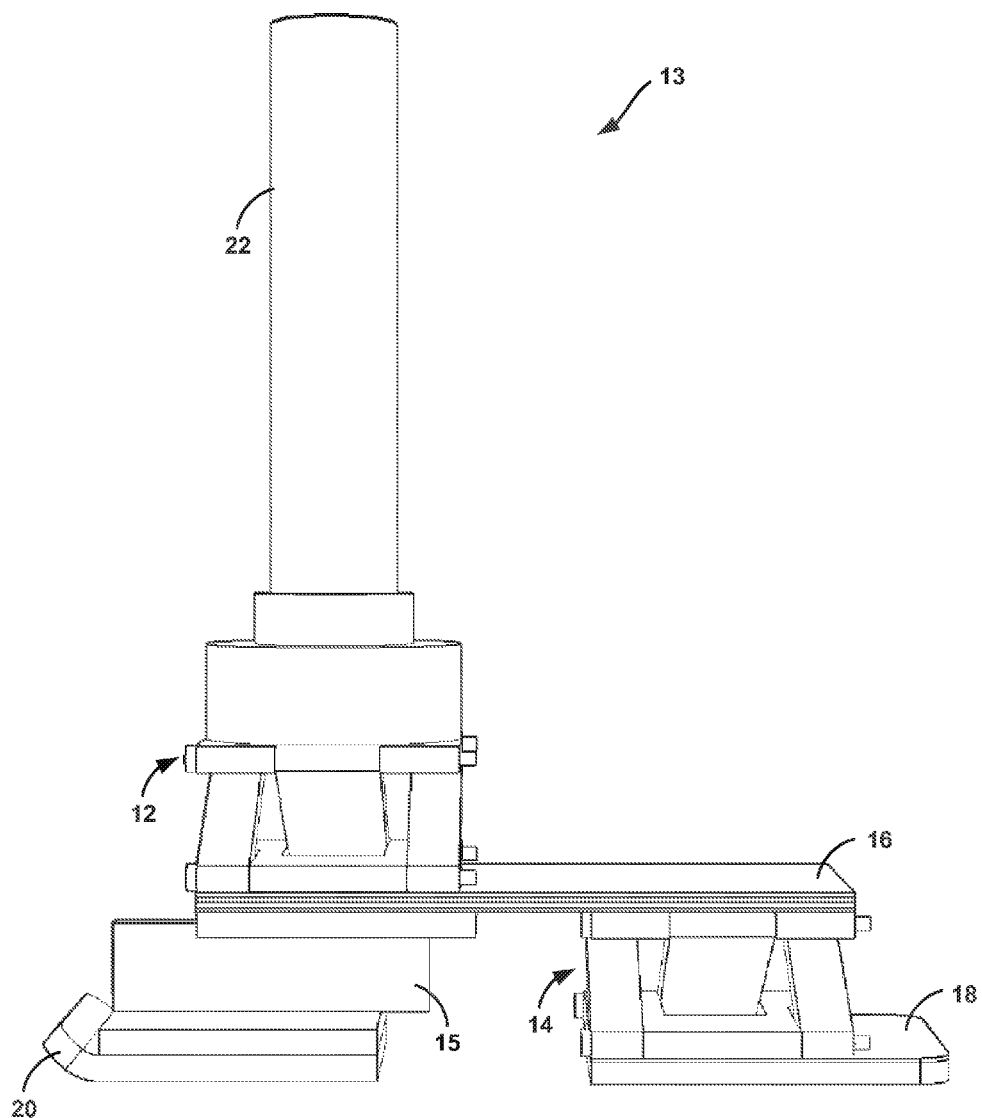
FIG. 12 is a side view of the prosthetic device, according to the example embodiment of FIG. 9.
Figure 13:
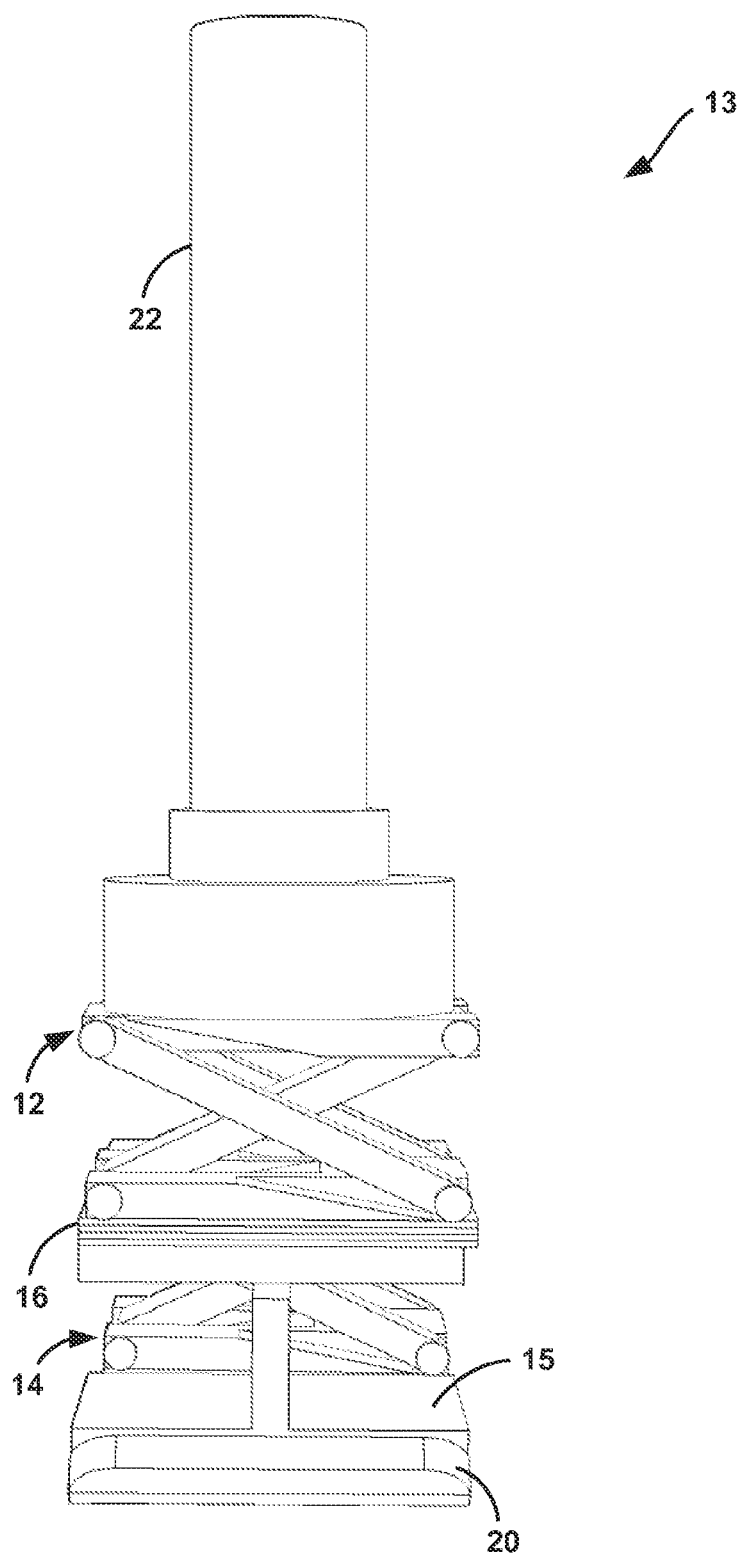
FIG. 13 is a rear view of the prosthetic device, according to the example embodiment of FIG. 9.

FIG. 11 illustrates a front view of the prosthetic device 13, including the first linkage system 12, the second linkage system 14, the flexible bridging platform 16, the flexible strut 18 and the prosthetic limb 22. FIG. 12 illustrates a side view of the prosthetic device 13, including the first linkage system 12, the second linkage system 14, the hindfoot support 15, the flexible bridging platform 16, the flexible strut 18, the hindfoot pad 20 and the prosthetic limb 22. Similarly, FIG. 13 illustrates a rear view of the prosthetic device 13, including the first linkage system 12, the second linkage system 14, the hindfoot support 15, the flexible bridging platform 16, the hindfoot pad 20 and the prosthetic limb 22.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

I claim:

1. A device comprising:
   a first linkage system, a second linkage system, and a third linkage system, each linkage system including:
   (i) an upper support;
   (ii) a lower support;
   (iii) a cross bar linkage including a first cross bar and a second cross bar, wherein the first cross bar is configured with a first end pivotally coupled to a first end of the lower support and a second end pivotally coupled to a second end of the upper support, and wherein the second cross bar is configured with a first end pivotally coupled to a second end of the lower support and a second end pivotally coupled to a first end of the upper support;

a flexible bridging platform coupled to the upper support of the first linkage system and coupled to the upper support of the second linkage system, wherein the plane of rotation of the lower support of the first linkage system is substantially parallel to the plane of rotation of the lower support of the second linkage system, and wherein the lower support of the third linkage system is coupled to the flexible bridging platform, wherein the plane of rotation of the lower support of the third linkage system is substantially perpendicular to the plane of rotation of the lower support of the first and second linkage systems; and a flexible strut coupled to the lower support of the second linkage system.

2. The device of claim 1, wherein the lower support of the first linkage system is coupled to a hindfoot pad, and wherein the flexible strut comprises a forefoot pad coupled to the lower support of the second linkage system and a flexible toe pad extending from the lower support of the second linkage system in a direction away from the first linkage system.

3. The device of claim 1, wherein the second linkage system has a shorter length and a shorter unweighted height than the length and unweighted height of the first linkage system.

4. The device of claim 1, wherein the cross bar linkage of each of the first linkage system, the second linkage system, and the third linkage systems further comprises a third cross bar, wherein the third cross bar of each of the first linkage system and the second linkage system is configured with a first end pivotally coupled to the first end of the lower support and a second end pivotally coupled to the second end of the upper support, and wherein the second cross bar is arranged in between the first cross bar and the third cross bar.

5. The device of claim 1, wherein the flexible bridging platform comprises a carbon fiber, a carbon fiber composite, a nylon material, or combinations thereof.

6. The device of claim 1, wherein the upper support of the third linkage system is configured to be coupled to a prosthetic limb.

7. The device of claim 1, wherein a maximum angle between the upper support of the first linkage system and the lower support of the first linkage system is between ten and twenty degrees.

8. The device of claim 1, wherein a maximum angle between the upper support of the second linkage system and the lower support of the second linkage system is between twenty-five and thirty-five degrees.

9. The device of claim 1, wherein a maximum angle between the upper support of the third linkage system and the lower support of the third linkage system is between twenty-five and thirty-five degrees.

10. The device of claim 1, further comprising a housing sized and shaped to receive the device.

11. A prosthetic foot device comprising:
a hindfoot support;
an ankle support including a first linkage system;
a forefoot support including a second linkage system, wherein each of the first linkage system and the second linkage system comprise:
(i) an upper support;
(ii) a lower support;
(iii) a cross bar linkage including a first cross bar and a second cross bar, wherein the first cross bar is configured with a first end pivotally coupled to a first end of the lower support and a second end pivotally coupled to a second end of the upper support, and wherein the second cross bar is configured with a first end pivotally coupled to a second end of the lower support and a second end pivotally coupled to a first end of the upper support; and
a flexible bridging platform, wherein a top surface of the flexible bridging platform is coupled to the lower support of the first linkage system, and wherein a bottom surface of the flexible bridging platform is coupled to the upper support of the second linkage system and an upper surface of the hindfoot support, and wherein the plane of rotation of the lower support of the first linkage system is substantially parallel to the plane of rotation of the lower support of the second linkage system.

12. The prosthetic foot device of claim 11, wherein the second linkage system has a shorter length and a shorter unweighted height than the length and unweighted height of the first linkage system.

13. The prosthetic foot device of claim 11, wherein the length to unweighted height ratio of the first linkage system is less than 2:1, and wherein the length to unweighted height ratio of the second linkage system is less than 2:1.

14. The prosthetic foot device of claim 11, wherein the hindfoot component includes a third linkage system including a spring mechanism configured to return the third linkage system to a position of repose when the prosthetic foot device is unweighted.

* * * * *